US 6,702,561 B2

(12) United States Patent
Stillig et al.

(10) Patent No.: US 6,702,561 B2
(45) Date of Patent: Mar. 9, 2004

(54) DEVICES FOR POTTING A FILTER FOR BLOOD PROCESSING (75) Inventors: Martin Stillig, Dransfeld (DE); Jeffrey H. Burbank, Boxford, MA (US); James M. Brugger, Newburyport, MA (US)

(73) Assignee: NxStage Medical, Inc., Lawrence, MA (US)

( * ) Notice: Subject to any disclaimer, the term of this patent is extended or adjusted under 35 U.S.C. 154(b) by 58 days.

(21) Appl. No.: 09/904,712

(22) Filed: Jul. 12, 2001

(65) Prior Publication Data
US 2003/0010702 A1 Jan. 16, 2003

(51) Int. Cl.[7] .......................... B29C 41/04; B29C 41/20
(52) U.S. Cl. ............... 425/120; 210/321.8; 210/321.89; 264/261; 264/279; 264/DIG. 48; 425/127; 425/425
(58) Field of Search ................... 210/321.6, 321.8, 210/321.89; 264/310, 311, 271.1, 279, 261, 263, DIG. 48; 425/110, 120, 127, 425

(56) References Cited

U.S. PATENT DOCUMENTS

| 3,442,002 | A | * | 5/1969 | Geary, Jr. et al. ............. 29/450 |
|---|---|---|---|---|
| 4,047,563 | A | | 9/1977 | Kurata |
| 4,190,411 | A | * | 2/1980 | Fujimoto ..................... 425/434 |
| 4,201,673 | A | | 5/1980 | Kanno et al. |
| 4,227,295 | A | * | 10/1980 | Bodnar et al. .............. 29/527.3 |
| 4,497,104 | A | * | 2/1985 | Fowles et al. .............. 29/419.1 |
| 4,617,161 | A | * | 10/1986 | Rollins et al. .............. 264/136 |
| 5,480,552 | A | | 1/1996 | Soltys et al. |
| 5,556,591 | A | * | 9/1996 | Jallerat et al. .............. 264/516 |
| 5,882,516 | A | | 3/1999 | Gross et al. |
| 5,955,353 | A | * | 9/1999 | Amiot ..................... 435/297.4 |
| 6,074,559 | A | | 6/2000 | Hahmann et al. |

FOREIGN PATENT DOCUMENTS

| WO | WO 00/44478 A1 | 8/2000 |
|---|---|---|
| WO | WO 00/53293 A1 | 9/2000 |

* cited by examiner

Primary Examiner—Robert Davis
(74) Attorney, Agent, or Firm—Proskauer Rose LLP (57) ABSTRACT A device for potting a filter is described. The device comprises a housing having a first hole in the first region communicating between the surface and the lumen, and a second hole in the second region communicating between the surface and the lumen. A ridge extends around the first hole and the second hole to define a trough for receipt of a flowable potting material. During the manufacture of the filter assembly, the housing is rotated about an axis that bisects the housing and is perpendicular to an axis of the lumen, a flowable material is placed on the surface of the housing, a portion of the flowable material flows toward the first hole, is retained by the ridge, and passes through the first hole, and a portion of the flowable material flows toward the second hole, is retained by the ridge, and passes through the second hole.

33 Claims, 6 Drawing Sheets

DEVICES FOR POTTING A FILTER FOR BLOOD PROCESSING

FIELD OF THE INVENTION

The present invention relates generally to devices and methods useful in potting a filter for use in blood processing, such as hemofiltration, hemodialysis, hemodiafiltration, apherisis, hemoconcentration, and hemo-ultrafiltration. More specifically, the devices and methods provide even distribution of potting material at the ends of the filter.

BACKGROUND OF THE INVENTION

Dialysis has prolonged the lives of patients with acute or chronic renal insufficiency. In hemodialysis, for example, a semi-permeable membrane or filter is used to remove unwanted substances from the blood while adding desirable components by the process of diffusion across the filter. Fluid removal during dialysis is partially determined by (1) the hydrostatic pressure changes, and (2) the dialysis membranes that have differing ultrafiltration coefficients, i.e., fluid removed per millimeters of mercury pressure per minute. The principal dialyzer used in the United States is the hollow fiber or capillary dialyzer. In the hollow fiber or capillary dialyzer, membrane material is spun into fine capillaries and thousands of these capillaries are packed into bundles. Blood flows through the capillaries while dialysate is circulated on the outside of the fiber bundle.

Membranes or filters used in hemofiltration, hemodialysis, hemodiafiltration, apherisis, hemoconcentration, and hemo-ultrafiltration are prepared in a similar fashion. Potting material, such as polyurethane, is used to bond the membrane fibers within the dialyzer housing. However, even distribution of the potting material along the filter capillaries is difficult to achieve.

What is needed are devices and methods that can be used to evenly distribute potting material along the fiber membrane for use during hemofiltration, hemodialysis, hemodiafiltration, apherisis, hemoconcentration, and hemo-ultrafiltration.

SUMMARY OF THE INVENTION

The present invention provides devices and methods that allow even distribution of potting material along the ends of the filter fibers for use in blood processing procedures. In one embodiment, the device comprises a cylindrical-shaped housing with an outer surface and a hollow lumen. One hole near one end of the housing communicates between the outer surface and the hollow lumen. A second hole at the other end of the housing also communicates between the outer surface and the hollow lumen. The housing includes a ridge in the outer surface that extends around the first hole and around the second hole. The ridge takes the form of a trough and acts to guide flowable material through the first hole and through the second hole when flowable material flows toward the holes.

In use, the housing is packed with filter fiber membrane in the hollow lumen, and is covered at each end. A containment cover is placed over the trough. The housing is then rotated about an axis that bisects the housing and is perpendicular to the longitudinal axis of the lumen of the housing. A flowable potting material, e.g., polyurethane, is placed on the outer surface of the housing off center about halfway between the first hole and the second hole. As the housing spins, the flowable potting material divides into two portions, such that one portion flows toward the first hole, and a second portion flows toward the second hole. The ridge acts as a backstop behind each hole. The ridge retains the flowable material and guides the flowable material through each of the first and second holes.

The flowable material then passes into the hollow lumen of the housing and distributes between the filter fibers. Centrifugal force impels the flowable potting material toward the ends of the filter fibers until it contacts the ends of the housing. In this manner, flowable potting material is evenly distributed to each end of the housing and filter fibers. The flowable potting material is then allowed to harden by curing, thereby bonding the fibers. The housing and filter fibers are then cut at each end to open the fibers closed by the urethane and to form a smooth surface that will receive and/or pass blood. The filter or dialyzer is completed by attaching a cap on each end of the cylindrical housing.

In another method, the filter fibers are placed in the housing and the trough with a dam feature is filled with urethane. The housing is then spun, forcing the urethane over the dam by centrifugal force into the first and second holes. The urethane then passes into the hollow lumen of the housing and distributes between the filter fibers. After the urethane is allowed to harden and bond the fibers, the ends of the housing and fibers are cut to form a smooth surface and a cap is attached on each end of the housing.

It will be understood that there will be several advantages to using the devices and methods described herein for distribution of potting material. These advantages include (1) ease and efficiency of distributing potting material due to elimination of step of potting in a separate housing, (2) reduced expense of manufacturing, (3) precise control of even distribution of potting material; and (4) elimination of a separately molded component for delivery of the potting material by having a built-in trough.

DETAILED DESCRIPTION

Figure 1:
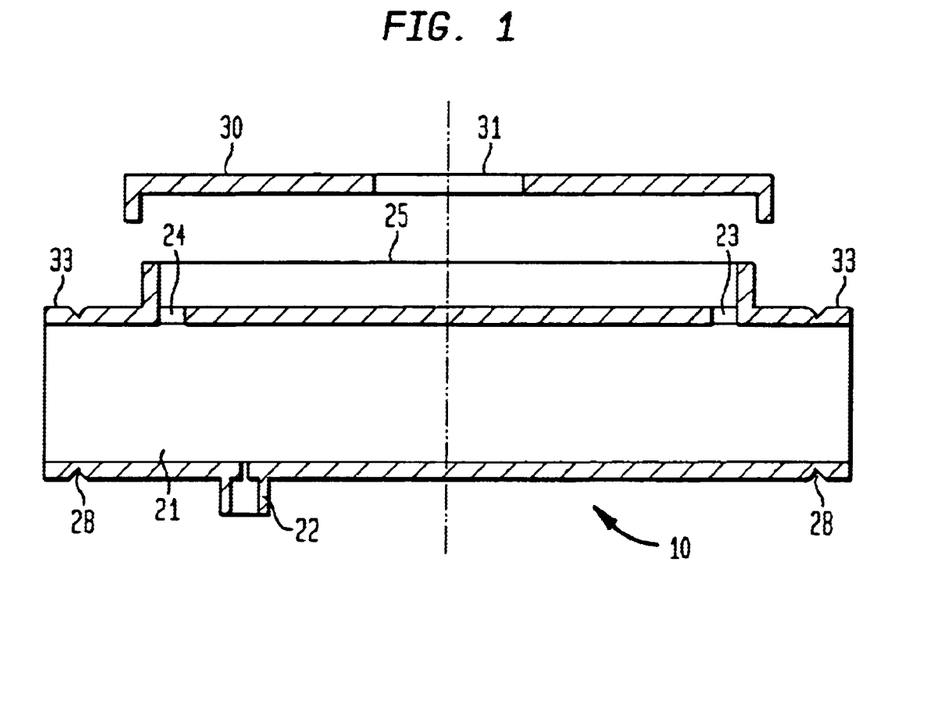
FIG. 1 depicts a longitudinal cross-sectional view of a filter housing for blood processing in accordance with the present invention.

A housing with a potting distribution trough according to the present invention is shown in FIG. 1. Housing 10, typically of a cylindrical shape or of some other suitable geometry, has hollow lumen 21 and at least one ultrafiltrate port 22. Housing 10 includes first hole 23 and second hole 24, one at each end of the housing, communicating between the outer surface of the housing and hollow lumen 21. Ridge 25 is mounted on the outer surface of the housing and extends around first hole 23 and second hole 24 to act as a backstop behind each hole. Ridge 25 extends around first hole 23 to a point closer the first end of the housing and extends around hole 24 to a point closer the second end of the housing. Containment cover 30 with hole 31 may be placed over ridge 25 to prevent spillage of a flowable material, e.g., urethane, when the housing is rotated. The urethane is injected off center through hole 31 for even distribution. In certain embodiments, notch 28 is included at each end of housing 10 and serves as a guide to cut the housing to remove end portion 33, a portion of membrane filter fibers, and a portion of potting material after completion of the potting distribution process described herein.

Figure 1A:
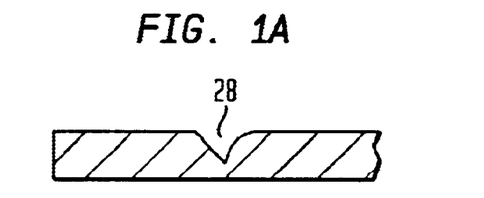
FIG. 1A depicts an enlargement of a portion of the end of the housing shown in FIG. 1.
Figure 2:
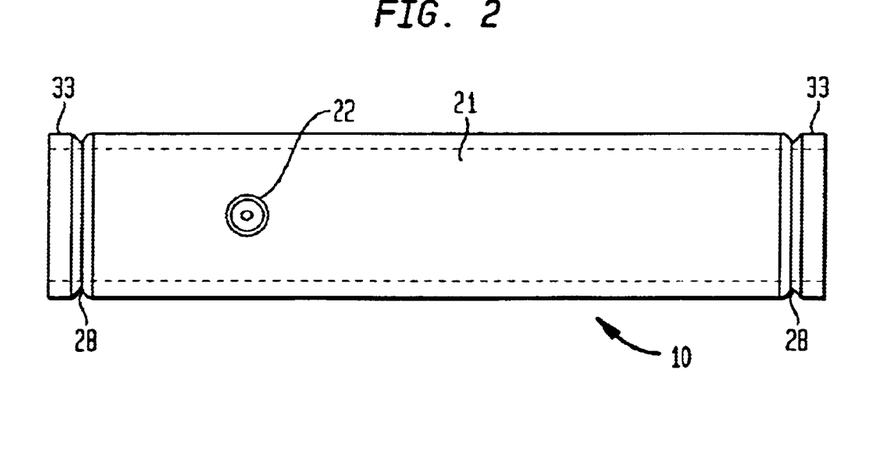
FIG. 2 depicts a side view of the housing of FIG. 1 showing an ultrafiltrate port.
Figure 3:
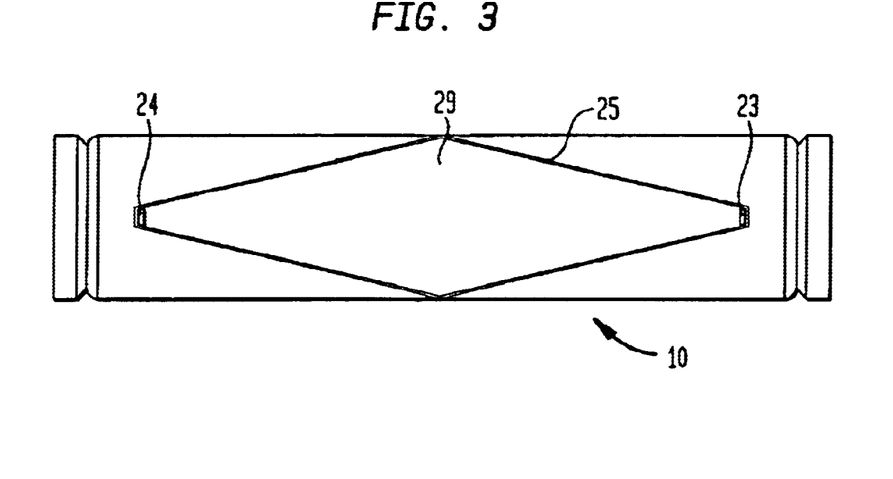
FIG. 3 depicts a side view of the housing of FIG. 1 showing a potting distribution trough.
Figure 3A:
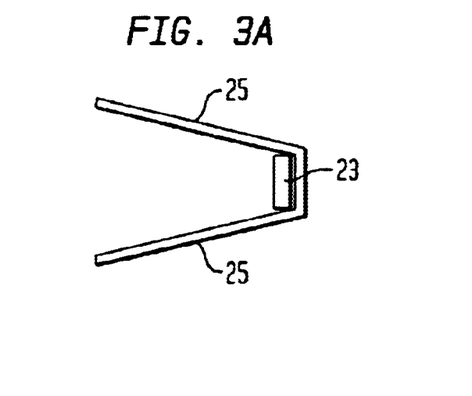
FIG. 3A depicts an enlargement of a portion of the potting distribution trough depicted in FIG. 3.

FIG. 1A depicts an enlarged view of notch 28 which will generally extends around the circumference of housing 10 at each end of the housing. FIG. 2 depicts a side view of the housing of FIG. 1 having ultrafiltrate port 22. FIG. 3 depicts another side view of the housing of FIG. 1 showing the potting distribution trough. First hole 23 and second hole 24 communicates between the outer surface of the housing and the hollow lumen. Ridge 25 extends just outside of the first and second holes at the outermost portion of the ridge. At the center of housing 10, ridge 25 forms widened region 29 for receiving a flowable material, typically a flowable potting material such as polyurethane. In one embodiment, ridge 25 is arranged in the shape of a parallelogram, and preferable diamond-shaped. FIG. 3A depicts an expanded view of ridge 25 and first hole 23, which may optionally be rectangular or any other suitable geometry, e.g., a square.

Figure 4:
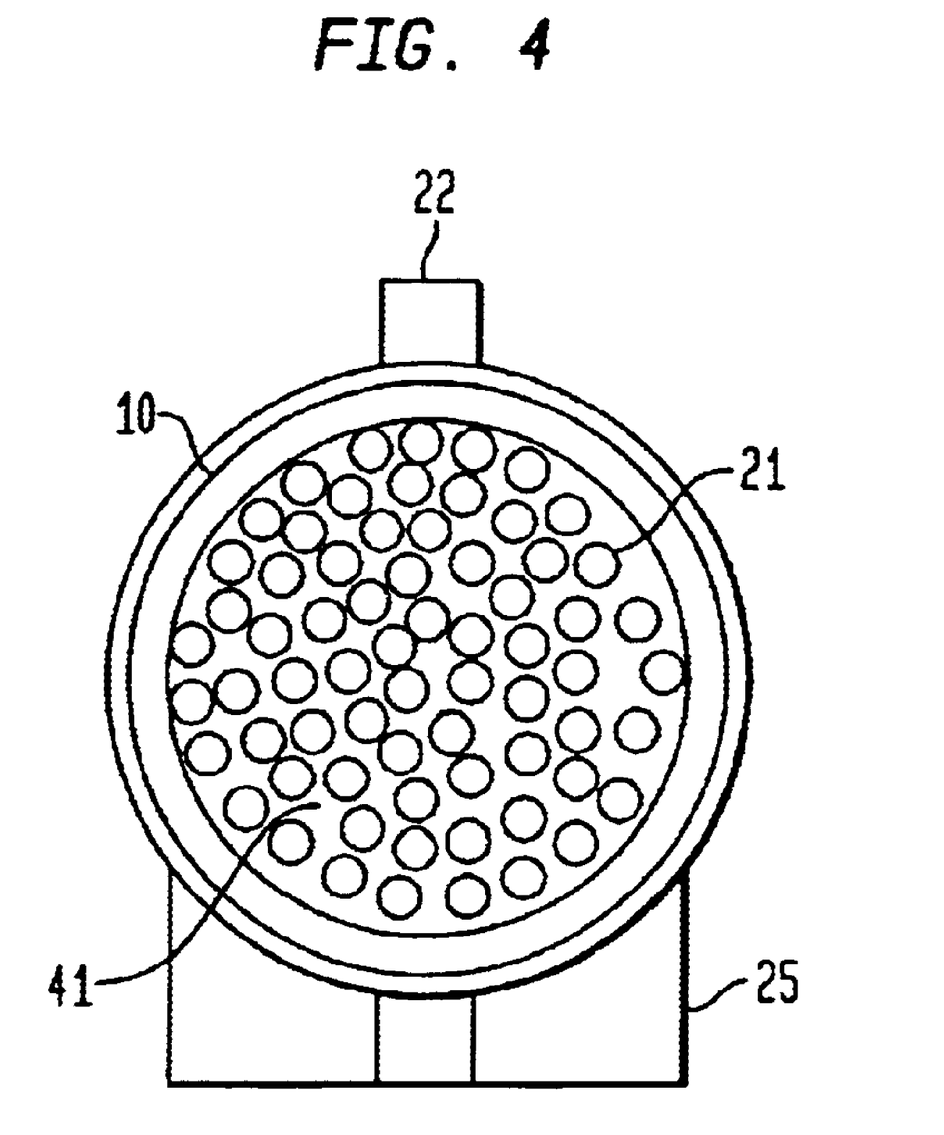
FIG. 4 depicts an end view of the housing and fiber membrane after removing an end portion of the housing.

FIG. 4 shows an end view of housing 10 after removal of end portion 33. The ends of filter fibers 41 are visible and fixed within cured potting material 11 that fills the ends of lumen 21 of housing 10. Ultrafiltrate port 22 and trough ridge 25 are also visible in this end view.

Figure 5A:
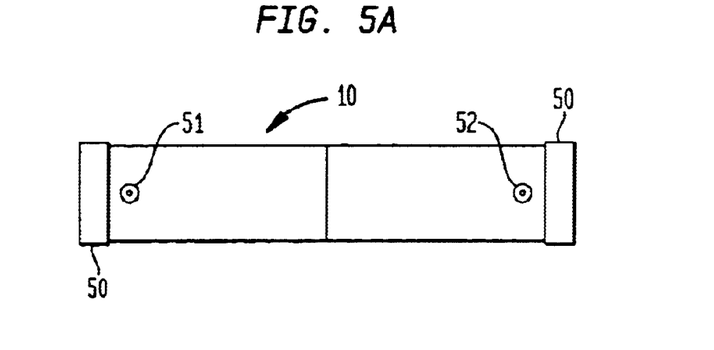
FIG. 5A depicts a side view of a housing for hemodiafiltration in accordance with the present invention.
Figure 5B:
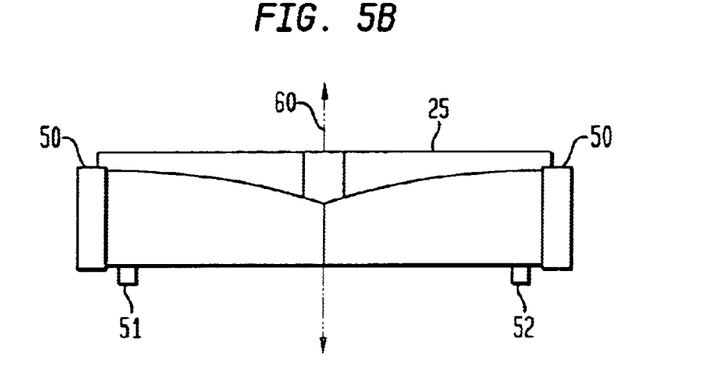
FIG. 5B depicts a side view of the housing of FIG. 5A showing a potting distribution trough.
Figure 5C:
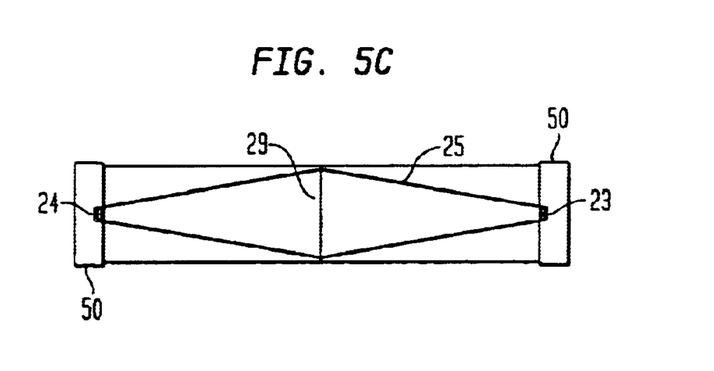
FIG. 5C depicts another side view of the housing of FIG. 5A showing a potting distribution trough.

FIG. 5A depicts another embodiment of a housing with potting distribution trough for preparation of a hemodiafiltration or hemodialysis filter. Housing 10 is equipped with dialysate entry port 51 and dialysate exit port 52. The housing is packed with fiber membrane and each end is covered with caps 50 before commencing potting distribution. FIG. 5B shows a side view of the housing depicted in FIG. 5A. Potting ridge 25 is visible on one side of housing 10. FIG. 5C depicts another side view of the housing showing the distribution trough and holes 23 and 24.

In use, housing 10 is rotated about axis 60 (see FIG. 5B) that bisects the cylindrical housing and is perpendicular to an axis of the hollow lumen. A flowable material, typically a flowable potting material, e.g., polyurethane, is placed on the outer surface of the housing within trough 25 within region 29, approximately halfway between first hole 23 and second hole 24. A portion of the flowable potting material flows toward first hole 23, is retained by ridge 25 and passes through hole 23 into hollow lumen 21. A second portion of the flowable potting material flows toward second hole 24, is retained by ridge 25 and passes through second hole 24 into hollow lumen 21. Centrifugal force impels the flowable potting material toward each end of housing 10 and toward the ends of fiber membrane 41 where the flowable potting material is retained by first and second caps 50. The potting material is allowed to harden by curing. End portions 33 of housing 10 are cut along notches 28 to produce a smooth surface that will receive and/or pass blood.

Figure 6:
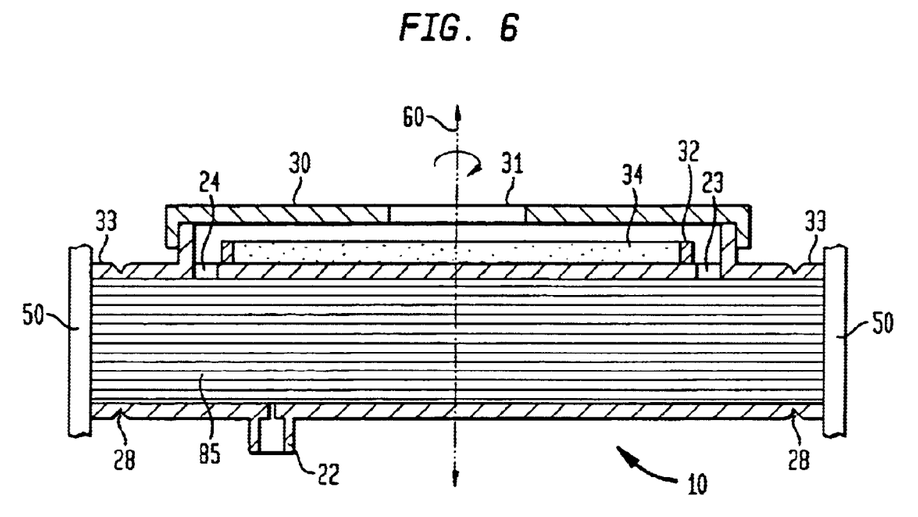
FIG. 6 depicts another embodiment of the potting distribution trough having a potting dam.
Figure 7:
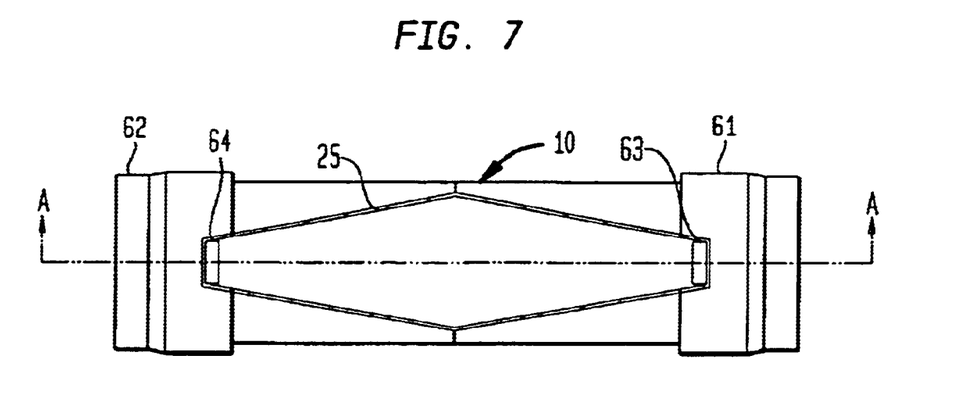
FIG. 7 depicts another side view of the housing of FIG. 5A having a cap at each end of the housing.
Figure 7A:
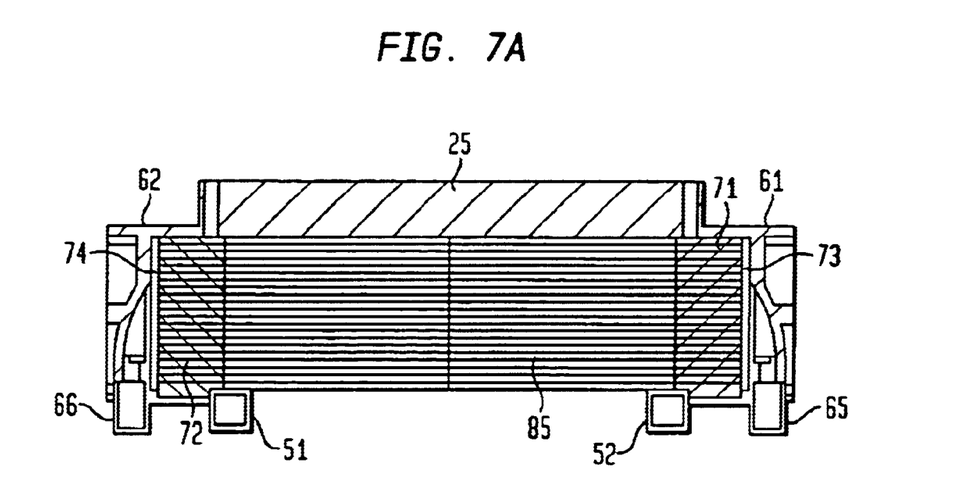
FIG. 7A depicts a longitudinal cross-sectional view of the housing of FIG. 6 through section line A—A.

FIG. 6 depicts another embodiment of the potting distribution trough having potting dam 32. In use, housing 10 is rotated about axis 60, and polyurethane 34 is injected through hole 31 of containment cover 30 into dam 32. Under centrifugal force, a portion of the polyurethane flows over the dam toward first hole 23 and second hole 24, and is retained by ridge 25 into hollow lumen 21. Centrifugal force further impels the polyurethane toward each end of housing 10 and toward the ends of fiber membrane 41 where the polyurethane is retained by first and second caps 50. The potting material is allowed to harden by curing. End portions 33 of housing 10 are cut along notches 28 to produce a smooth surface that will receive and/or pass blood. Blood inlet cap 61 and blood outlet cap 62 are then installed on opposite ends of housing 10 as depicted in FIG. 7. In certain embodiments, cap 61 has notch 63 and cap 62 has notch 64, where each notch is shaped to fit around the ends of potting trough 25. FIG. 7A depicts a longitudinal cross-sectional view of the housing of FIG. 7 taken through section line A—A. Filter fibers 85 are contained in the cylindrical housing. Blood inlet cap 61 includes inlet port 65 that is in fluid communication with headspace 73 adjacent potting material 71. Blood outlet cap 62 includes outlet port 66 that is in fluid communication with headspace 74 adjacent potting material 72. In other embodiments, blood inlet cap 61 and blood outlet cap 62 further include hemodilution ports as described in U.S. Applications Ser. No. 09/904,709, filed Jul. 12, 2001, entitled HEMODILUTION CAP AND METHODS OF USE IN BLOOD-PROCESSING PROCEDURES, incorporated by reference herein in its entirety. With reference to FIG. 1, the inner diameter of the hollow lumen may be approximately 30–60 mm, more preferably approximately 45–50 mm, more preferably approximately 47 mm. The distance between first hole 23 and the first end of housing 10 may be approximately 15–25 mm, more preferably approximately 21 mm. Bond socket 22 may be approximately 0.25 inches. The distance between the two notches 28 may be approximately 20–30 cm, more preferably approximately 23–27 cm, more preferably approximately 25 cm. The distance between ultrafiltrate port 22 and the nearest end of the housing may be approximately 25–40 mm, more preferably approximately 36 mm. With reference to FIG. 1A, first notch 28 may be located approximately 8–12 mm from the first end of housing 10, more preferably approximately 10 mm from the first end of housing 10, while second notch 28 is located approximately 8–12 mm from the first end of housing 10, more preferably approximately 10 mm from the first end of housing 10. With reference to FIG. 3A, the thickness of trough 25 may be approximately 0.5–2 mm, more preferably approximately 1 mm. The width of rectangular hole 23 may be approximately 1–3 mm, more preferably approximately 2 mm. The length of rectangular hole 23 may be approximately 5–9 mm, more preferably approximately 7 mm. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. For example, it will be understood that any feature of any device or method disclosed herein can be used with any of the other devices or methods, even though any given figure might depict only a particular combination.

What is claimed is:

1. A device for potting a filter, comprising: a housing having a first end, a second end, an outer surface, an inner surface, a hollow lumen, a first region near the first end, a second region near the second end, a first hole in the first region communicating between the outer surface of the housing and the hollow lumen, and a second hole in the second region communicating between the outer surface of the housing and the hollow lumen; and a ridge on the outer surface of the housing that extends around the first hole to a point closer the first end of the housing and extends around the second hole to a point closer the second end of the housing, the ridge defining a trough having a continuous access defined by said ridge, said ridge having an edge adapted to seal against a separate cap such that during filter manufacturing, the housing and cap are rotated about an axis that bisects the housing and is perpendicular to an axis of the lumen, a flowable material is placed on the outer surface of the housing approximately halfway between the first hole and the second hole, a portion of the flowable material flows toward the first hole, is retained by the ridge and said separate cap, and passes through the first hole, and a portion of the flowable material flows toward the second hole, is retained by the ridge and said separate cap, and passes through the second hole.

2. The device of claim 1, wherein the housing is a cylindrical-shaped housing.

3. The device of claim 1, further comprising a first cap on the first end of the cylindrical housing and a second cap on the second end of the cylindrical housing.

4. The device of claim 1, further comprising filter membrane fibers within the hollow lumen of the housing.

5. The device of claim 1, further comprising an ultrafiltrate port in the housing communicating between the outer surface of the housing and the inner lumen.

6. The device of claim 3, wherein the first cap includes a blood inlet port and the second cap includes a blood outlet port.

7. The device of claim 6, wherein the first cap further comprises an hemodilution port and the second cap further comprises a hemodilution port.

8. A device for potting a filter, comprising: a housing having a first end, a second end, an outer surface, an inner surface, a hollow lumen, a first region near the first end, a second region near the second end, a first hole in the first region communicating between the outer surface of the housing and the hollow lumen, and a second hole in the second region communicating between the outer surface of the housing and the hollow lumen; and a ridge on the outer surface of the housing that extends around the first hole to a point closer the first end of the housing and extends around the second hole to a point closer the second end of the housing, wherein, during filter manufacturing, the housing is rotated about an axis that bisects the housing and is perpendicular to an axis of the lumen, a flowable material is placed on the outer surface of the housing approximately halfway between the first hole and the second hole, a portion of the flowable material flows toward the first hole, is retained by the ridge, and passes through the first hole, and a portion of the flowable material flows toward the second hole, is retained by the ridge, and passes through the second hole wherein the ridge is a generally diamond-shaped parallelogram.

9. The device of claim 1, further comprising a first cutting notch in the first region extending around the circumference of the housing, and a second cutting notch in the second region extending around the circumference of the housing.

10. The device of claim 1, wherein the first and second holes are rectangular shaped.

11. A device for potting a filter, comprising:

a filter housing configured to hold filter membrane fibers extending along a length thereof between first and second ends of said filter housing;

said filter housing having at least one first opening at said first end and at least one second opening at said second end, said at least one first opening and said at least one second opening communicating with an interior of said filter housing with a flow guide for guiding the flow of potting material;

said flow guide having a ridge connected alone a length of said filter housing such that said flow guide has the shape of an open trough;

said flow guide being configured such that potting material flows toward said holes when said flow guide is temporarily covered to enclose it by a cap and when said filter housing and said cap are spun about an axis perpendicular to a longitudinal axis of said filter housing, whereby when filter fibers are held in said filter housing and potting material so caused to flow, the amount of potting material settling toward said first and second ends is maximized.

12. The device of claim 11, wherein said guide is channel-shaped.

13. The device of claim 11, wherein said guide is configured such that equal amounts of potting material are caused to flow to each of said openings.

14. The device of claim 11, wherein said channel and said openings are configured such that said potting material may include polyurethane.

15. The device of claim 11, wherein said flow guide is an integral part of said filter housing.

16. The device of claim 15, wherein said guide is channel-shaped.

17. A device for potting a filter, comprising:

means for supporting filter fibers;

means for containing potting material at ends of said means for supporting;

means for guiding permanently attached to said means for supporting a fluid effective to seal said filter fibers when said fluid is hardened;

means for temporarily enclosing an open length of said means for guiding, said means for guiding including means for conveying said fluid toward said means for containing such that said fluid is distributed evenly between said ends when said means for supporting, said means for guiding, and said means for temporarily enclosing are spun about an axis of said means for supporting.

18. A device as in claim 17, wherein said means for supporting is configured to form a flow plenum of a filter.

19. A device as in claim 17, wherein said means for supporting is a filter housing.

20. A device as in claim 17, wherein said means for containing include respective interiors and said means for conveying include openings in communication with said interiors.

21. A device for potting a filter, comprising:

a generally cylindrical housing with a hollow lumen and a trough defined by a ridge running longitudinally along an axis of said housing;

said ridge extending from said generally cylindrical housing such that said trough is closed on all sides except for a trough opening facing away from said housing except for at least one opening near each end of said housing communicating an interior of said trough with an interior of said housing;

said ridge having an edge adapted to seal against a separate cap thereby defining an enclosure such that during filter manufacturing, when the housing and said separate cap are rotated about a spinning axis, which is perpendicular to said housing axis, with a flowable material placed in said trough, said separate cap keeps said flowing material from flowing over said ridge, thereby causing said flowing material to flow into said openings, retained by the ridge and separate cap.

22. A device as in claim 21, wherein said ridge has an edge surrounding said trough opening, said edge lies in a plane, said trough is wider toward a center thereof than at its ends, said ridge following said cylindrical housing such that said trough is also deeper toward said center.

23. A device as in claim 21, wherein said ridge defines a parallelogram shape.

24. A device as in claim 21, wherein said trough has a bottom surface opposite said trough opening whose surface follows a shape of said housing.

25. A device as in claim 23, wherein said trough has a bottom surface opposite said trough opening whose surface is cylindrical.

26. A device for potting a filter, comprising:

a housing configured to hold a filter bundle, said housing having an elongated shape with a longitudinal axis;

said housing having an elongated open trough on a side thereof, said trough having a longitudinal axis generally parallel to said housing longitudinal axis;

said housing having at least one port communicating an interior of said housing with an exterior thereof;

said open trough being defined by a ridge having an edge;

said edge being shaped to form a seal with a trough cap such that said open trough may be enclosed.

27. A device as in claim 26, wherein said trough has openings communicating said interior of said trough with an interior of said housing.

28. A device as in claim 26, wherein said ridge defines a parallelogram.

29. A device as in claim 26, wherein said ridge has an edge surrounding said trough opening, said edge lies in a plane, said trough is wider toward a center thereof than at its ends, said housing is generally cylindrical, and said ridge follows a shape said cylindrical housing such that said trough is also deeper toward said center.

30. A device as in claim 28, wherein said ridge defines a parallelogram.

31. A device as in claim 26, wherein said trough has a bottom surface opposite said trough opening whose surface follows a shape of said housing.

32. A device as in claim 26, further comprising end caps fittable on ends of said housing.

33. A device as in claim 26, further comprising filter membrane fibers within the hollow lumen of the housing.

* * * * *